(12) United States Patent
Otsuka et al.

(10) Patent No.: US 10,213,251 B2
(45) Date of Patent: Feb. 26, 2019

(54) HIGH-FREQUENCY TREATMENT TOOL (71) Applicant: SUMITOMO BAKELITE CO., LTD., Tokyo (JP)

(72) Inventors: Wataru Otsuka, Akita (JP); Shinetsu Harata, Akita (JP)

(73) Assignee: SUMITOMO BAKELITE COMPANY LIMITED, Tokyo (JP)

( * ) Notice: Subject to any disclaimer, the term of this patent is extended or adjusted under 35 U.S.C. 154(b) by 448 days.

(21) Appl. No.: 14/787,815

(22) PCT Filed: May 30, 2014

(86) PCT No.: PCT/JP2014/064401
§ 371 (c)(1),
(2) Date: Oct. 29, 2015

(87) PCT Pub. No.: WO2014/196463
PCT Pub. Date: Dec. 11, 2014

(65) Prior Publication Data
US 2016/0113705 A1 Apr. 28, 2016

(30) Foreign Application Priority Data
Jun. 3, 2013 (JP) .................................. 2013-117058

(51) Int. Cl.
*A61B 18/14* (2006.01)
*A61B 18/00* (2006.01)
*A61B 17/00* (2006.01)

(52) U.S. Cl.
CPC ...... *A61B 18/1445* (2013.01); *A61B 18/1492* (2013.01); *A61B 2017/00526* (2013.01);
(Continued)

(58) Field of Classification Search
CPC . A61B 18/14; A61B 18/1442; A61B 18/1445; A61B 18/1448; A61B 18/1492;
(Continued)

(56) References Cited

U.S. PATENT DOCUMENTS

| 6,193,717 B1 | 2/2001 | Ouchi |
| 6,423,060 B1 | 7/2002 | Ouchi |

(Continued)

FOREIGN PATENT DOCUMENTS

| JP | 7-31587 A | 2/1995 |
| JP | 11-114059 A | 4/1999 |

(Continued)

OTHER PUBLICATIONS

International Search Report dated Jul. 29, 2014, issued in counterpart International Application No. PCT/JP2014/064401, w/Emglish translation (4 pages).

*Primary Examiner* — Michael Peffley
*Assistant Examiner* — Khadijeh Vahdat
(74) *Attorney, Agent, or Firm* — Westerman, Hattori, Daniels & Adrian, LLP (57) ABSTRACT

The high-frequency treatment tool includes a flexible tube inserted into a body cavity; an operating wire inserted through the flexible tube to be movable back and forth; a treatment part arranged on a distal end of the operating wire and treats biological tissue by applying a high-frequency current; a main body that fixes a base end of the flexible tube; a slider-fixing part that fixes a base end of the operating wire guided from the base end of the flexible tube and slides the operating wire in an axis direction with respect to the main body; and a slider-zipping part provided to encircle at least a portion of an outer peripheral surface of the slider-fixing part and slides the slider-fixing part by the operation of a user. The slider-fixing part is unrotatably coupled to the (Continued)

main body and the slider-gripping part is rotatably coupled to the slider-fixing part.

8 Claims, 8 Drawing Sheets

(52) U.S. Cl.
CPC ............... *A61B 2018/00196* (2013.01); *A61B 2018/00982* (2013.01)

(58) Field of Classification Search
CPC ........... A61B 2017/00526; A61B 2018/00196; A61B 2018/00982
USPC ...................................................... 606/41–52
See application file for complete search history.

(56) References Cited

U.S. PATENT DOCUMENTS

| | | |
|---|---|---|
| 2009/0036737 A1 | 2/2009 | Muyari |
| 2012/0046661 A1 | 2/2012 | Ishii et al. |
| 2012/0053595 A1 | 3/2012 | Nakao |

FOREIGN PATENT DOCUMENTS

| | | |
|---|---|---|
| JP | 2009-034388 A | 2/2009 |
| JP | 2009-247876 A | 10/2009 |
| WO | 2010/134273 A1 | 11/2010 |

FIG. 6

HIGH-FREQUENCY TREATMENT TOOL

TECHNICAL FIELD

The present invention relates to a high-frequency treatment tool and a method of assembling the same.

Priority is claimed on Japanese Patent Application No. 2013-117058, filed Jun. 3, 2013, the content of which is incorporated herein by reference.

BACKGROUND ART

High-frequency treatment tools are known in which a conductive treatment part is provided on a distal end of a flexible pipe. An operator operates an operating part provided on a base end of the pipe to make the treatment part reach an affected part of biological tissue, and further operates the treatment part to perform treatment of the biological tissue.

CITATION LIST

Patent Literature

[PTL 1] Japanese Unexamined Patent Application, First Publication No. 2009-247876

SUMMARY OF INVENTION

Technical Problem

A user operates an operating part which in turn rotates a pipe within a body cavity or pushes the pipe into the body cavity. In order to make a treatment part works, the operating part is operated such that an operating wire inserted into the pipe is moved hack and forth. In this case, if the user tries to rotate the entire pipe, operations of first loosening the gripping for moving the operating wire back and forth and gripping the operating wire again after rotation is required, which become a hindrance to continuous operation.

Solution to Problem

According to an aspect of the invention, a high-frequency treatment tool is provided, including: a flexible tube that is inserted into a body cavity; an operating wire that is inserted through the flexible tube so as to be movable back and forth; a treatment part that is arranged on a distal end of the operating wire and treats biological tissue by applying a high-frequency current; a main body that fixes a base end of the flexible tube; a slider-fixing part that fixes a base end of the operating wire guided from the base end of the flexible tube and slides the operating wire in an axis direction with respect to the main body; and a slider-gripping part that is provided so as to encircle at least a portion of an outer peripheral surface of the slider-fixing part and slides the slider-fixing part by the operation of a user, in which the slider-fixing part is unrotatably coupled to the main body and the slider-gripping part is rotatably coupled to the slider-fixing part.

In addition, the outline of the above invention does not enumerate all required features of the invention. Additionally, sub-combinations of these characterizing groups can also become inventions.

DESCRIPTION OF EMBODIMENTS

Hereinafter, although the invention will be described through an embodiment of the invention, the following embodiment does not limit the invention related to the claims. Additionally, all combinations of features described in the embodiment are not indispensable for solving means of the invention.

Figure 1:
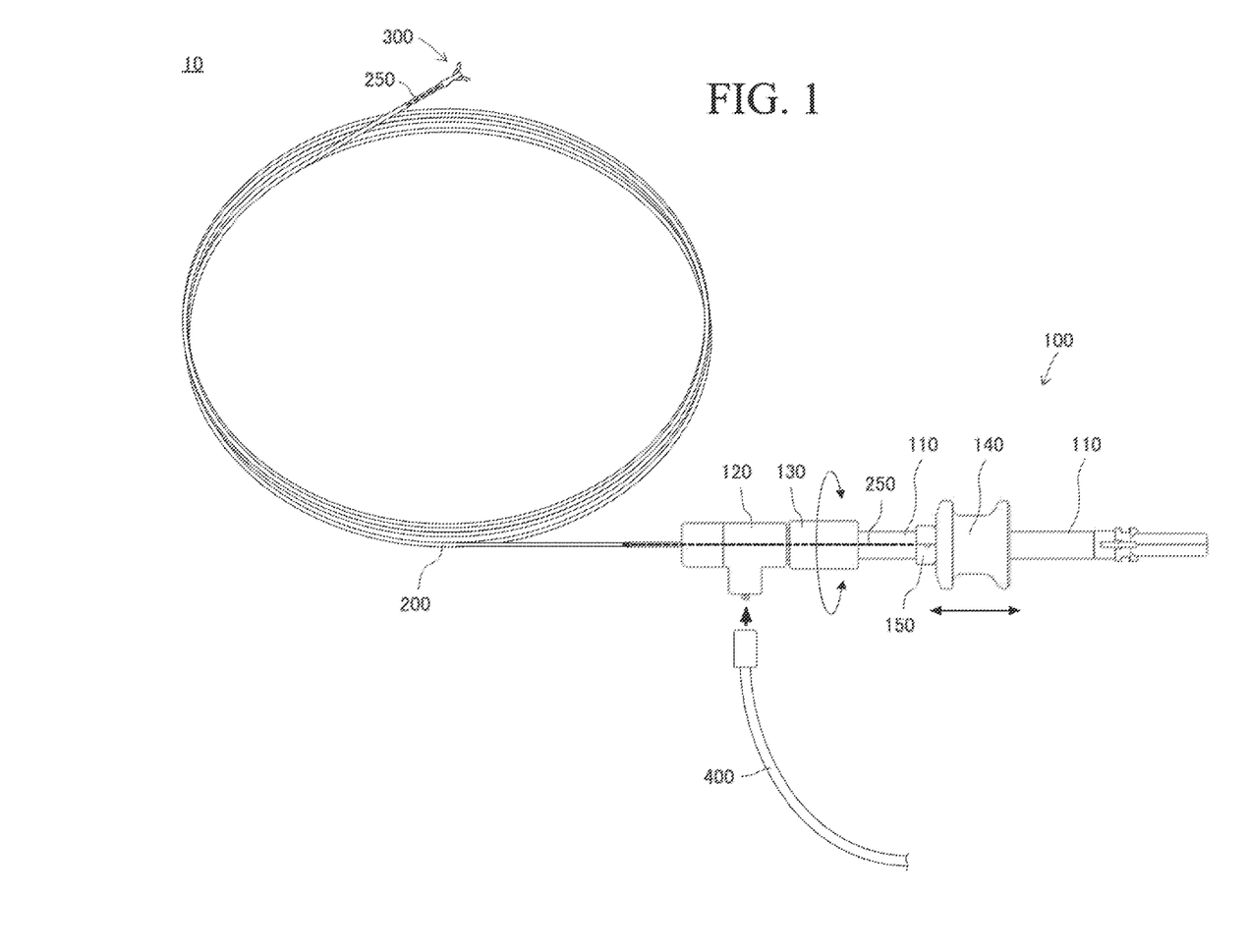
FIG. 1 is a view illustrating an overall configuration of a high-frequency treatment tool related to the present embodiment.

FIG. 1 is a view illustrating an overall configuration of a high-frequency treatment tool 10 related to the present embodiment. The high-frequency treatment tool 10 related to the present embodiment is a monopolar high-frequency treatment tool for endoscopes. The high-frequency treatment tool 10 mainly includes an operating part 100 that users, such as a doctor, operate outside the body of, for example, a subject, such as a diseased person, a flexible tube 200 that is, for example, a sheath inserted into and removed from a treatment tool guide pipe of an endoscope, and a treatment part 300 that treats an affected part of biological tissue within a body cavity. In addition, in the present embodiment, description will be made with the treatment part 300 side of the high-frequency treatment tool 10 defined as a distal end and the operating part 100 side defined as a base end. Additionally, targets to be treated are not limited to affected parts, and may be normal biological tissue that can be included as targets for pathological examination or the like.

The operating part 100 includes a main body 110, a terminal part 120, a main body-operating part 130, a slider-gripping part 140, and a slider-fixing part 150 as constituent parts. The main body 110 is formed in a substantially columnar shape, and is rotatably connected to a base end of the flexible tube 200 introduced thereinto from an end surface of the column. Therefore, even if a user rotates the main body 110 around a column axis, the flexible tube 200 does not rotate in the following manner. An operating wire 250 is inserted through the flexible tube 200 so as to be movable back and forth. A central axis of the operating wire 250 is arranged so as to substantially coincide with the column axis of the main body 110 in the operating part 100. Thus, in the present embodiment, description will be made with a direction along the central axes being defined as an axis direction. A base end of the operating wire 250 is fixed inside the main body 110. Therefore, if the user rotates the main body 110 around the column axis, the operating wire 250 receives the acting force and rotates inside the flexible tube 200 in the following manner.

A power cord 400 that supplies electric power to the treatment part 300 is attached to and detached from the terminal part 120. Although described below in detail, the terminal part 120 is rotatably coupled to the main body 110.

Therefore, even if the main body 110 has been rotated around the axis by the user, the power cord 400 can maintain its initial posture without rotating with this rotation. That is, the power cord 400 is not wound around the main body 110.

The main body-operating part 130 is a grip part that is formed to be larger than the diameter of a column section of the main body 110, that is, becomes a thick shaft so as to be easily gripped when the user rotates the main body 110. Therefore, the main body-operating part 130 is coupled unrotatably to the main body 110, that is, is coupled to the main body 110 so as not to rotate relatively. By forming the main body-operating part 130 so as to become a thick shaft, the user can rotate the main body 110 with a smaller force. Particularly since the user often wears rubber gloves when using the high-frequency treatment tool 10, it is also effective for reducing slipping in that the main body 110 can be rotated with a smaller force.

The slider-gripping part 140 and the slider-fixing part 150 form a double structure in which the slider-gripping part 140 is located outside the main body 110 and the slider-fixing part 150 is located inside the main body 110. The slider-gripping part 140 is a grip part to be gripped by the user. The slider-fixing part 150 fixes the base end of the operating wire 250 guided from the base end of the flexible tube 200.

The slider-gripping part 140 and the slider-fixing part 150 move integrally in the axis direction. Therefore, if the user slides the slider-gripping part 140 in the axis direction, the slider-fixing part 150 also slides in the axis direction. In this case, the operating wire 250 fixed to the slider-fixing part 150 slides in the axis direction with respect to the main body 110. Since the flexible tube 200 is fixed to the main body 110, the operating wire 250 moves back and forth inside the flexible tube 200 if the user slides the slider-gripping part 140. That is, if the user slides the slider-gripping part 140 toward the base end, the operating wire 250 slides inside the flexible tube 200 toward the base end, and conversely, if the user slides the slider-gripping part 140 toward the distal end, the operating wire 250 slides inside the flexible tube 200 toward the distal end.

The flexible tube 200 is inserted into the treatment tool guide pipe of the endoscope as described above, or is directly inserted into a body cavity, and plays a role of making the treatment part 300 reach biological tissue to be targeted. Additionally, the flexible tube 200 also plays a role of transmitting electric power, which is supplied from the power cord 400, to the treatment part 300. The flexible tube 200 has rigidity and flexibility for which the mutual balance among a push-in property relating to insertion, the turning force transmission performance of reliably transmitting a turning force from the hands to the distal end, and bending resistance in which bending does not occur is taken into consideration. A specific configuration will be described below.

The treatment part 300 is opened and closed by the forward and backward movement of the operating wire 250. For example, bleeding is stopped by pinching biological tissue using the treatment part 300 to apply a high-frequency current.

Figure 2:
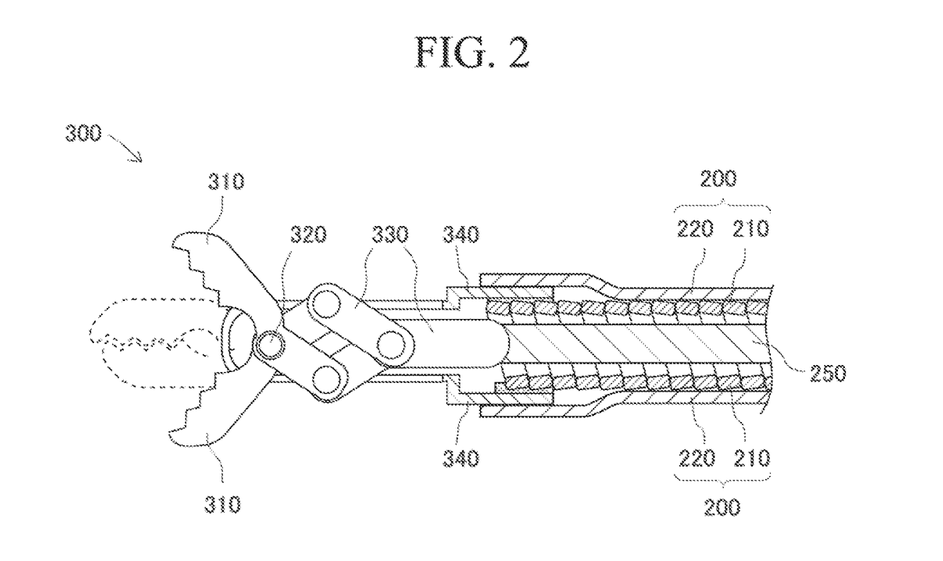
FIG. 2 is a view illustrating a partial section in the vicinity of a treatment part.

FIG. 2 is a view illustrating a partial section in the vicinity of the treatment part 300. Specifically, FIG. 2 is a sectional view including the axis of the operating wire 250, and a mechanism at a distal end is illustrated as a front view for ease of understanding.

The flexible tube 200 has a coil pipe 210 as a skeletal structure that extends from a base end fixed to the main body 110 to the distal end as illustrated. The coil pipe 210 is a coil in which a coil element wire is spirally wound, the space inside the spiral is hollow, and both ends are formed as openings. The operating wire 250 slides by moving back and forth in the space inside the spiral. Conductive materials are used as the coil element wire, and for example, copper, iron, aluminum, nickel, and their alloys (stainless steel, brass, and the like) are candidates. Although the coil element wire is a round wire of which the cross-sectional shape may be circular, a flat wire of which the cross-sectional shape is a rectangular shape may be used in order to make the diameter of the flexible tube 200 small.

The coil pipe 210 functions as a conductive part that realizes rigidity and flexibility for which the balance among the above-described push-in property, turning force transmission performance, and bending resistance is taken into consideration, as the skeletal structure, and guides electric power, which is supplied from the power cord 400, to the treatment part 300.

The flexible tube 200 has a coating layer 220 that covers an outer peripheral surface of the coil pipe 210 to form an outermost layer. As the coating layer 220, insulating materials having excellent slidability can be used, and, for example, polytetrafluoroethylene (PTFE), tetrafluoroethylene hexafluoropropylene copolymer (FEP), polyvinyl alcohol (PVA), and polyvinyl pyrrolidone can be used.

The treatment part 300 is mainly constituted of a treatment electrode 310, a supporting shaft 320, a link mechanism 330, and a supporting frame 340. The treatment electrode 310 is a scissors type electrode consisting of two parts. The supporting shaft 320 has both ends fixed to the supporting frame 340, and pivotally supports the treatment electrode 310 at a trunk thereof so as to allow rocking and sliding. The supporting shaft 320 is formed of a conductive member. The link mechanism 330 connects a force point of the treatment electrode 310 and the distal end of the operating wire 250.

The supporting frame 340 is a cap member that covers and fixes an outer peripheral surface of a distal end of the coil pipe 210 in an annular shape, and fixes and supports both ends of the supporting shaft 320. The supporting frame 340 is formed of, for example, a metallic conductive member, and is fixed to the outer peripheral surface of the distal end of the coil pipe 210 by welding, brazing, or the like. Accordingly, the supporting shaft 320 and the supporting frame 340 electrically connect the treatment electrode 310 and the coil pipe 210.

The supporting frame 340 has a slit from a portion where the link mechanism 330 rocks to the distal end in which the treatment electrode 310 opens and closes. The treatment electrode 310 is brought into an open state as illustrated if the link mechanism 330 is pushed in the direction of the distal end by the operating wire 250, and is brought into a closed state as illustrated by dotted lines if the link mechanism 330 is pulled in the direction of the base end by the operating wire 250.

Figure 3A:
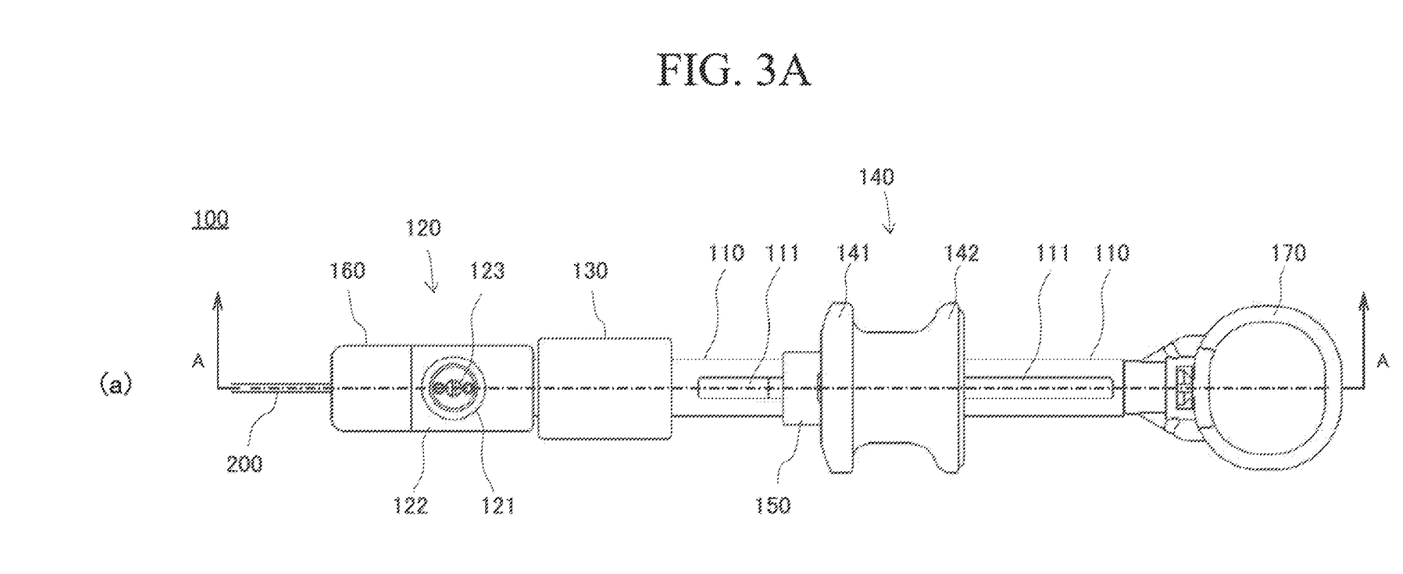
FIG. 3A is a top view of the external appearance of an operating part.
Figure 3B:
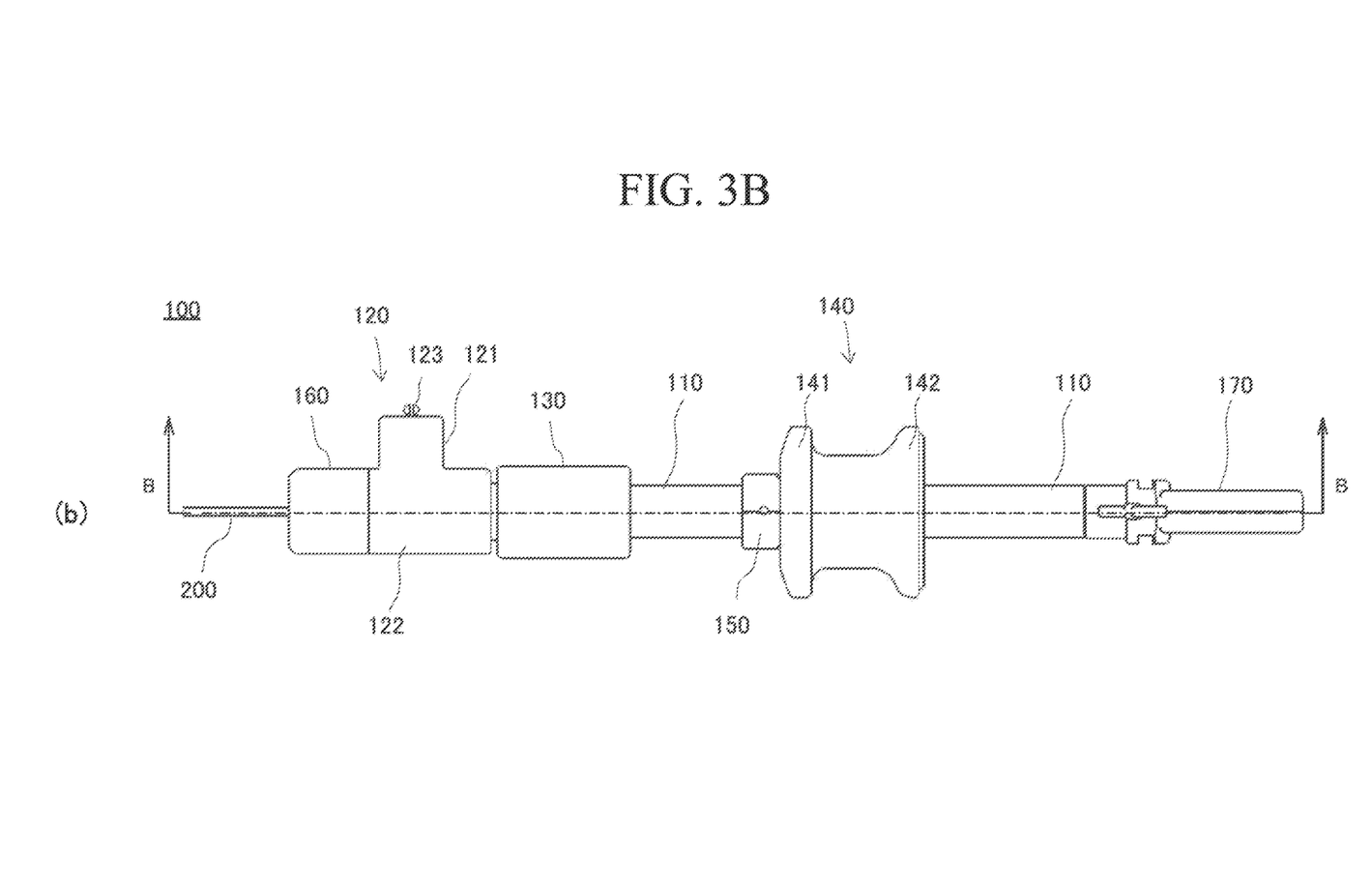
FIG. 3B is a front view of the external appearance of the operating part.

Next, the operating part 100 will be described in detail. FIGS. 3A and 3B are external appearance views of the operating part 100. Particularly, FIG. 3A is a top view, and FIG. 3B is a front view.

The terminal part 120 is coupled to a distal end of the main body 110 so as to be rotatable with respect to the main body 110. Moreover, the distal end of the main body is provided with a terminal cover 160 that blocks a distal end opening of the terminal part 120 with an inlet of the flexible tube 200 being left. The main body 110 is formed of, for example, polyoxymethylene (POM). In addition, if moldability, slidability, insulation, strength, and the like are satisfied, various materials, such as acrylonitrile-styrene copolymer (AS), acrylonitrile-butadiene-styrene copolymer (ABS), and polyphenylsulfone (PPSU), can be adopted. Additionally, various materials can also be adopted for the terminal cover 160, similar to the main body 110.

The terminal part 120 is constituted of a connecting portion 121 that receives the power cord 400, and a rotating portion 122 that forms a columnar shape coaxial with the main body 110. The connecting portion 121 forms a columnar shape orthogonal to the rotating portion 122. A power supply terminal 123 electrically connected to the power cord 400 is provided inside the connecting portion 121. If the power cord 400 is mounted on and locked to the connecting portion 121, the power cord 400 can be freely rotated with the terminal part 120 around the axis with respect to the main body 110. In other words, the main body 110 can be freely rotated around the axis with the posture of the terminal part 120 on which the power cord 400 is mounted being kept constant. That is, since the main body 110 slidingly rotates around the axis with respect to the terminal part 120 that is stationary, the power cord 400 does not become wound around the main body 110. Various materials can also be adopted as the terminal part 120, similar to the main body 110.

A slit hole 111 is provided along the axis direction in the main body 110. Specifically, the slit hole 111, as illustrated in FIG. 3A, is an elongated hole that passes through the main body so as to include the axis from an upper surface toward a lower surface and that has the axis direction as a major axis. The slider-fixing part 150 can be guided by the slit hole 111 and moved in the axis direction. In other words, the movement range of the slider-fixing part 150 is limited depending on the length of the slit hole 111 in the axis direction.

As described above, the slider-gripping part 140 is overlappingly provided at the slider-fixing part 150 so as to encircle at least a portion of an outer peripheral surface of the slider-fixing part 150. The slider-gripping part 140 has two collars, i.e. a first collar 141 on the distal end and a second collar 142 at the base end. The each collar is formed so as to extend in a circumferential direction from a trunk that forms a cylindrical shape. By virtue of such a shape, the user can comfortably perform the sliding operation of the slider-fixing part 150 by pinching the trunk, for example, with his/her index finger and middle finger, and pushing out the first collar 141 toward the distal end or pushing in the second collar 142 toward the base end. Particularly, the user often wears rubber gloves when using the high-frequency treatment tool 10. However, such a sliding operation also has the advantage that slipping does not easily occur because an operating force can be received by the collars. Various materials can be adopted for the slider-gripping part 140 and the slider-fixing part 150, similar to the main body 110.

A finger-hooking portion 170 is coupled to the base end of the main body 110 so as to be rotatable with respect to the main body 110. The finger-hooking portion 170 forms an annular shape that has an internal diameter to such a degree that the user's thumb can be inserted therethrough. For example, if the user pinches the slider-gripping part 140 with his/her index finger and middle finger while inserting his/her thumb through the finger-hooking portion 170, the user can move his/her index finger and middle finger with respect to his/her thumb, and can more comfortably perform the sliding operation of the slider-fixing part 150. Various materials can also be adopted for the finger-hooking portion 170, similar to the main body 110.

The main body-operating part 130, as described above, is a grip part to be gripped when rotating the main body 110. For example, when the user grips and operates the slider-gripping part 140 with his/her right hand, the user grips the main body-operating part 130 with his/her left hand. Therefore, the main body-operating part 130 is provided in a portion different from a portion where the slit hole 111 is provided in the axis direction. In the present embodiment, the main body-operating part 130 is provided between the terminal part 120 and the slit hole 111. Various materials can also be adopted for the main body-operating part 130, similar to the main body 110. In addition, the main body-operating part 130 may be formed as a portion of the main body 110 by forming a portion of the main body 110 so as to become a thick shaft.

Figure 4A:
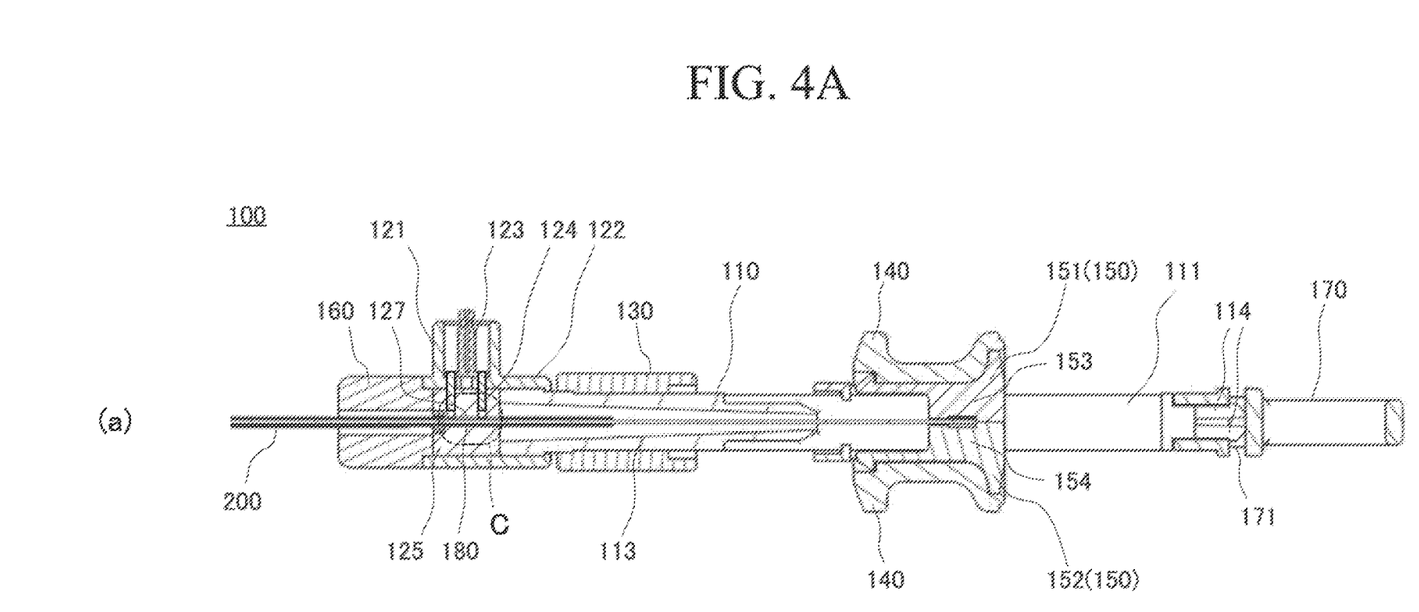
FIG. 4A is an A-A sectional view of the operating part.
Figure 4B:
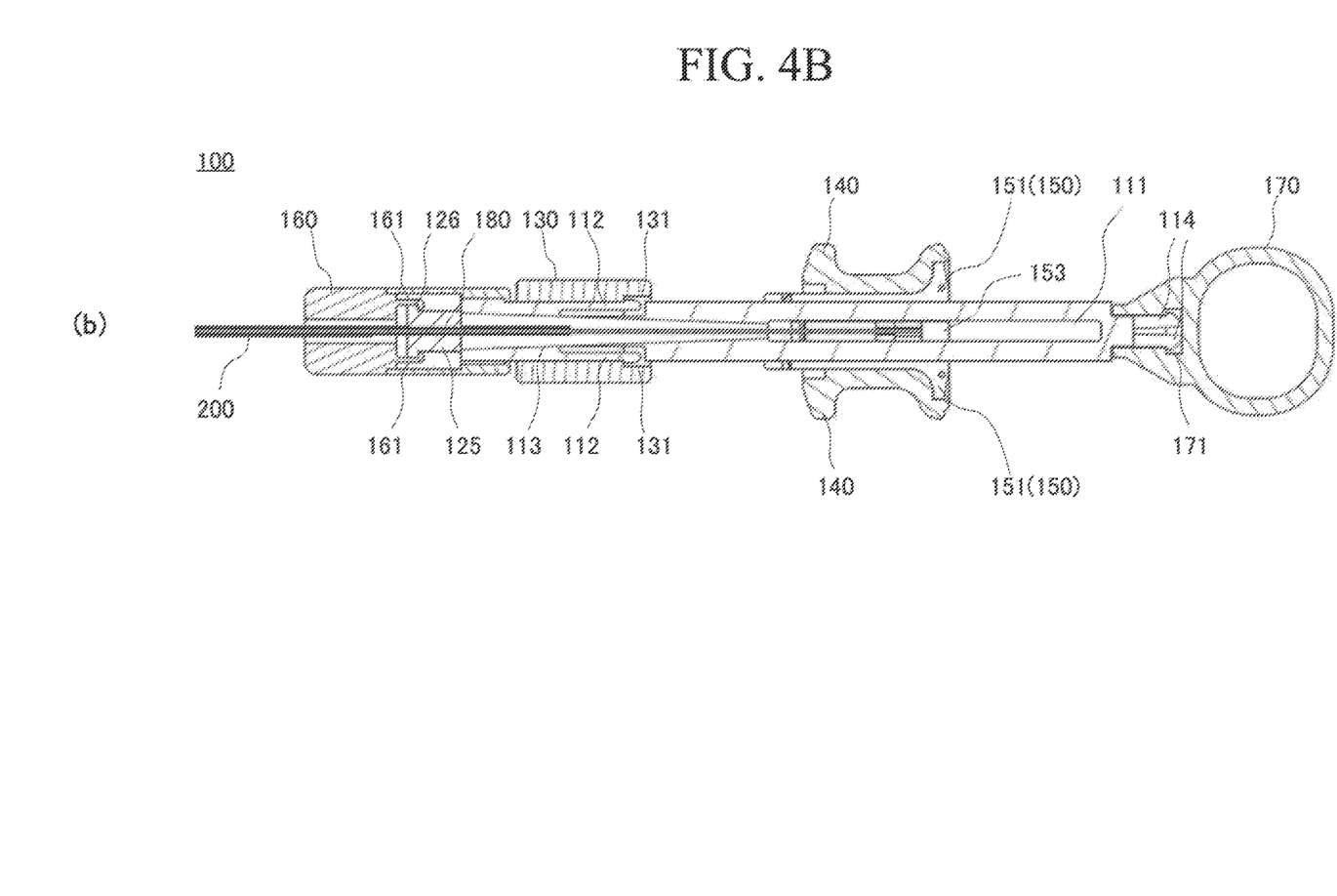
FIG. 4B is a B-B sectional view of the operating part.

FIGS. 4A and 4B are sectional views of the operating part 100. Particularly, FIG. 4A is an A-A sectional view of FIG. 3A, and FIG. 4B is a B-B sectional view of FIG. 3B.

As illustrated in FIG. 4A, the slider-fixing part 150 is constituted of two parts of a first fixing part 151 and a second fixing part 152. The first fixing part 151 has a first tab 153 inserted through the slit hole 111, and the second fixing part 152 similarly has a second tab 154 inserted through the slit hole 111. Specifically, the respective tabs are formed in a plate shape so as to guide sliding operation in accordance with the width of the slit hole 111.

The first tab 153 and the second tab 154 are inserted through, assembled into, and integrated with the slit hole 111 from opposite sides, respectively so that the first fixing part 151 and the second fixing part 152 form the slider-fixing part 150. In this case, a base end part of the operating wire 250 inserted along the central axis of the main body 110 is fixed inside the main body 110 by being sandwiched by the first tab 153 and the second tab 154.

In this way, the slider-fixing part 150 assembled to the slit hole 111 generally has a cylindrical portion coaxial with the main body 110 and a flange formed so as to extend in the circumferential direction from the cylindrical portion, as its entire external shape.

In contrast, the slider-gripping part 140 is formed as a cylindrical integral part. The slider-gripping part 140 is assembled so as to cover and encircle the slider-fixing part 150. The slider-gripping part 140 overlappingly assembled to the slider-fixing part 150 is rotatable around the cylindrical portion of the slider-fixing part 150. That is, the user can freely rotate the slider-gripping part 140 around the axis with respect to the slider-fixing part 150 that is restricted to be stationary by the slit hole 111 and the tabs. Additionally, the slider-gripping part 140 is formed to be thick so as to have such a degree of rigidity that the slider-gripping part does not deform due to the user's gripping force.

The base end of the main body 110 is formed with a plurality of base end hooks 114. Additionally, the finger-hooking portion 170 is formed with an inner groove 171. The finger-hooking portion 170 is rotatably coupled to the base end of the main body 110 by snap fitting in which a claw of the base end hook 114 is hung on the inner groove 171.

The main body 110 has an inner tube 113 that leads to the slit hole 111 from a distal end opening. The inner tube 113 is a hollow space through which the operating wire 250 and the flexible tube 200 are inserted. The inner tube 113 constitutes a funnel shape in which the diameter of the distal end opening is made larger so as to allow the operating wire 250 or the like to be easily inserted therethrough from the distal end opening.

The main body 110 has a plurality of outer peripheral hooks 112 on an outer peripheral side of the inner tube 113. The outer peripheral hooks 112 each have an arm along the axis direction, and a claw perpendicular to the axis direction, and, for example, two outer peripheral hooks are provided using the axis direction as an axis of symmetry. The main body-operating part 130 has an engaging groove 131 that engages with the claws of the outer peripheral hooks 112. The main body-operating part 130 assembled to the main body 110 along the axis direction is coupled to the main body 110 by the snap fitting in which the outer peripheral hooks 112 are engaged with the engaging groove 131, and slip-out thereof is prevented. Additionally, the engaging groove 131 restricts the claws of the outer peripheral hooks 112 such that the claws do not rotate around the axis. The main body-operating part 130 that is a gripping part that rotates the main body 110 is unrotatably attached to the main body 110 by virtue of such a structure.

For example, if the user grips and rotates the main body-operating part 130 with his/her left hand, the slit hole 111 also rotates around the axis. Since the slider-fixing part 150 is guided by the slit hole 111, the slider-fixing part 150 also rotates around the axis. Meanwhile, the user pinches the slider-gripping part 140 with the index finger and the middle finger of his/her right hand, for example, while inserting his/her thumb through the finger-hooking portion 170. In this case, as described above, since the slider-gripping part 140 and the finger-hooking portion 170 are rotatable with respect to the main body 110, the user can rotate the main body 110 with his/her left hand with the posture of his/her right hand maintained. In other words, even when the user rotates the main body 110 which in turn rotates the operating wire 250, the operation of first loosening the gripping of the slider-gripping part 140 and gripping the slider-gripping part 140 again is not required, and it is also not necessary to twist the gripping hand. Therefore, the continuous operation of rotating and sliding can be smoothly realized.

Additionally, the user will occasionally grasp the main body-operating part 130 and the slider-gripping part 140 with a strong force in the rotational operation of the main both 110. However, since the slider-gripping part 140 is formed to be thick, the sliding operation of the slider-fixing part 150 is not hindered even if the user grasps the sliding gripping part strongly. That is, the user can comfortably perform the rotational operation of the main body 110 and the sliding operation of the slider-fixing part 150 in parallel or independently even while the main body-operating part 130 and the slider-gripping part 140 are strongly gripped, respectively.

The terminal part 120 has the power supply terminal 123 erected inside the connecting portion 121, and the power supply terminal 123 is electrically connected to a fixing pin 124 extending toward the flexible tube 200. The fixing pin 124 is supported by and fixed to a terminal-fixing part 125 provided inside the rotating portion 122 of the terminal part 120. The terminal-fixing part 125 is fixed to the rotating portion 122 inside the rotating portion 122. The terminal-fixing part 125 has a through-hole 127 at a central portion thereof, and a conductive pipe 180 for allowing the flexible tube 200 to be inserted therethrough is inserted through the through-hole 127.

Although described below in detail, the terminal-fixing part 125 that supports and fixes the fixing pin 124 has conductivity, and plays a role in guiding electric power, which is supplied via the fixing pin 124, toward the conductive pipe 180. The conductive pipe 180 is, for example, a metallic pipe and is fixed to the main body 110. Since the conductive pipe 180 and the terminal-fixing part 125 are rotatable relative to each other, the terminal part 120 can be freely rotated with respect to the main body 110 as described above.

The terminal-fixing part 125 has a flange 126 on a distal end thereof, and engages with a hook 161 provided on the terminal cover 160. Accordingly, the terminal cover 160 is relatively fixed to the terminal part 120.

Figure 5A:
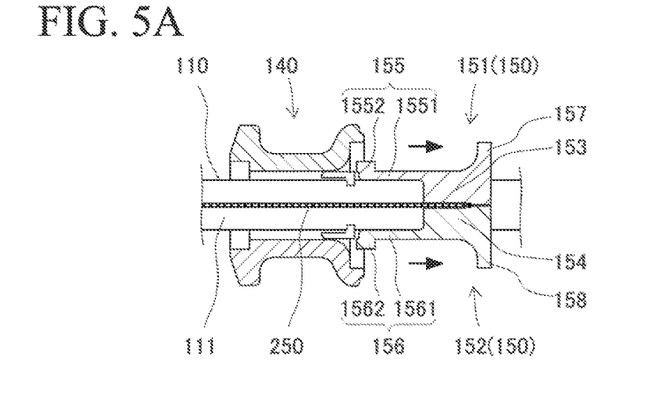
FIG. 5A is a view illustrating an assembling procedure of a slider-gripping part.
Figure 5B:
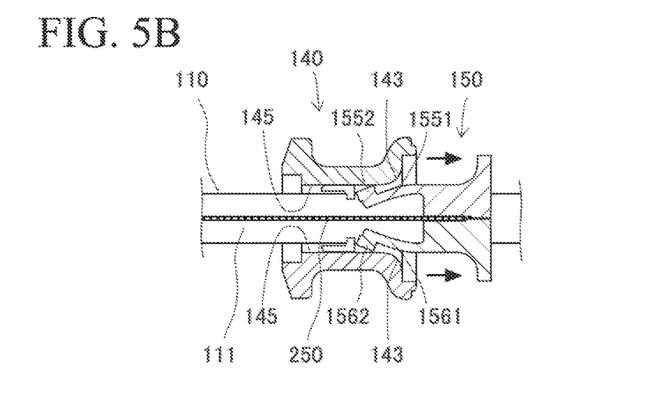
FIG. 5B is a view illustrating the assembling procedure of the slider-gripping part.
Figure 5C:
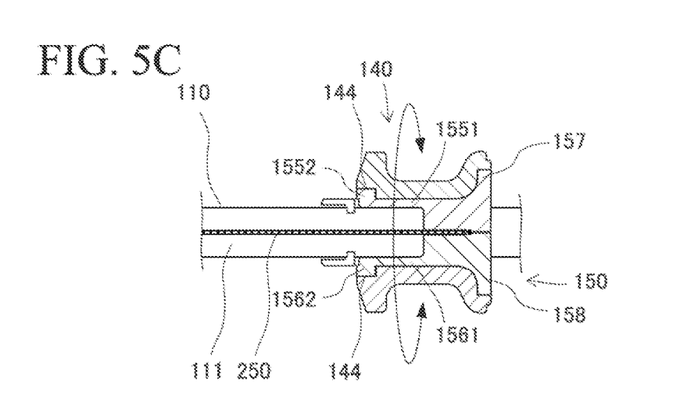
FIG. 5C is a view illustrating the assembling procedure of the slider-gripping part.

Next, an assembling procedure of assembling the slider-gripping part 140 to the slider-fixing part 150 will be described. FIGS. 5A, 5B, and 5C are views illustrating an assembling procedure of the slider-gripping part 140.

FIG. 5A illustrates that an inner cylinder of the slider-gripping part 140 is inserted through the main body 110 from the distal end and is made to approach the slider-fixing part 150. The first fixing part 151 has a first hook 155 extending toward the distal end along the axis direction. The first hook 155 consists of an arm 1551 and a claw 1552, and the arm 1551 can be bent (deformed) toward the operating wire 250, that is, toward the radial inner side of the slider-gripping part 140. Similarly, the second fixing part 152 has a second hook 156 extending toward the distal end along the axis direction. The second hook 156 consists of an arm 1561 and a claw 1562, and the arm 1561 can be bent (deformed) toward the operating wire 250, that is, toward the radial inner side of the slider-gripping part 140. In addition, since neither the first hook 155 nor the second hook 156 receives an external force in the state of FIG. 5A, a state where the hooks are parallel to the axis direction without being bent is maintained. Additionally, as illustrated, the operating wire 250 is already pinched by and fixed to the first tab 153 and the second tab 154 in a stage where the slider-gripping part 140 is assembled to the slider-fixing part 150.

FIG. 5B illustrates that the slider-gripping part 140 is made to approach the slider-fixing part 150 further and these parts overlap each other partially. If the claw 1552 of the first hook 155 and the claw 1562 of the second hook 156 are pressed in the extending direction of the operating wire 250, that is, toward the radial inner side of the slider-gripping part 140 while being brought into contact with and guided by an introducing portion 143 of the slider-gripping part 140, the arm 1551 and the arm 1561 begin to be bent in the direction concerned. Also, as illustrated, the claw 1552 and the claw 1562 come into sliding contact with an inner cylinder surface 145. In addition, the introducing portion 143 is a rounded portion or a tapered portion formed in a base end opening of the inner cylinder surface 145 of the slider-gripping part 140.

FIG. 5C illustrates that the slider-gripping part 140 is assembled to the slider-fixing part 150. If the base end opening of the slider-gripping part 140 reaches a first flange 157 formed on a base end of the first fixing part 151 and a second flange 158 formed on a base end of the second fixing part 152, further movement of the slider-gripping part 140 is restricted. Meanwhile, the claw 1552 and the claw 1562 that are coming into sliding contact with the inner cylinder surface 145 are fitted into the engaging groove 144 formed in a distal end opening of the slider-gripping part 140, and are increased in diameter and deformed radially outward, and bending of the arm 1551 and the arm 1561 is released. In other words, the claw 1552 and the claw 1562 function as locking parts that couple the slider-gripping part 140 and the slider-fixing part 150 together. The slider-gripping part 140 and the slider-fixing part 150 that have been engaged with each other by the snap fitting in this way are integrated with each other and become mutually immovable in the axis direction of the main body 110. It should be noted herein that the engaging groove 144 is formed over the whole circumference of the slider-gripping part 140, and movement of the claw 1552 and the claw 1562 is not restricted in the rotational direction. By virtue of such a configuration, the slider-gripping part 140 is allowed to rotate with respect to the slider-fixing part 150.

Figure 6:
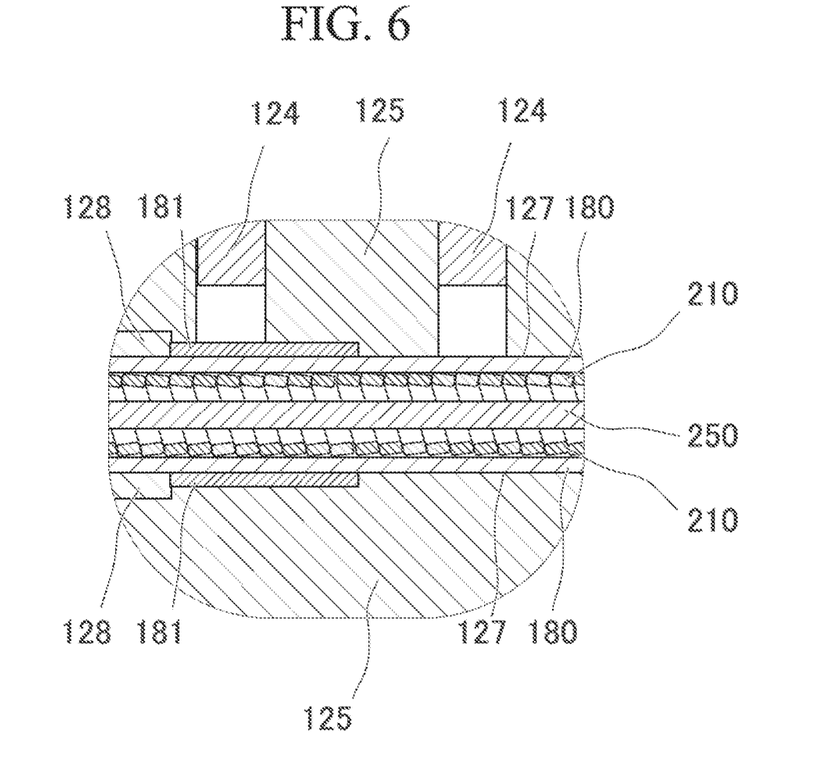
FIG. 6 is a partially enlarged view in the vicinity of a fixing pin.

Next, the vicinity of the distal end of the fixing pin 124 will be described. FIG. 6 is a partially enlarged view of the vicinity (portion C of FIG. 4A) of the fixing pin 124. A distal end of the fixing pin 124 is supported by and fixed to the terminal-fixing part 125 without reaching the conductive pipe 180. The conductive pipe 180 has a conductive sliding terminal 181 welded to a portion of an outer peripheral portion thereof. The sliding terminal 181 rotates integrally with the conductive pipe 180. The terminal-fixing part 125 is formed of the conductive materials as described above, and is arranged so as to always come into contact with the sliding terminal 181. Therefore, even if the terminal-fixing part 125 rotates relative to the sliding terminal 181 and the conductive pipe 180, the electrical connection with the sliding terminal 181 is steadily maintained. Hence, the electric power supplied from the fixing pin 124 can be stably supplied to the conductive pipe 180 via the sliding terminal 181. The coil pipe 210 through which the operating wire 250 is inserted is inserted through the conductive pipe 180. It should be noted herein that the coil pipe 210 is not covered with the coating layer 220 in the portion inserted through the conductive pipe 180, and comes into direct contact with the conductive pipe 180. Therefore, the electric power applied to the conductive pipe 180 is led to the coil pipe 210. The coil pipe 210 extends to the distal end as described above, and supplies electric power to the treatment electrode 310. In addition, a terminal-regulating part 128 restricting the axial movement of the sliding terminal 181 is provided on a distal end of the through-hole 127 of the terminal-fixing part 125. The terminal-regulating part 128 is formed of a conductive member, and is fixed to the terminal-fixing part 125.

Although the high-frequency treatment tool 10 as the monopolar high-frequency treatment tool for endoscopes related to the present embodiment has been described above, various variations of the configuration of the respective parts can be adopted. For example, the treatment electrode 310 can be mounted on various treatment tools without being limited to the scissors-shape. Additionally, although the coil pipe 210 serving as the skeletal structure of the flexible tube 200 is the conductive part that electrically connects the treatment part 300 and the conductive pipe 180 together, skeletal structures made of different materials can be used with providing circuit patterns.

The configuration in which the slider-fixing part 150 slides is not limited to the configuration in which the tabs are inserted through and guided by the slit hole 111, and other guide configurations may be adopted. Additionally, in the present embodiment, the engagement using the snap fitting in a plurality of places has been adopted. However, fixing methods using screws, bonding, and the like may be adopted.

Additionally, the high-frequency treatment tool 10 may be not of the monopolar type but of a bipolar type. When the high-frequency treatment tool is of the bipolar type, for example, a configuration in which two conductive lines are inserted into the flexible tube 200 may be adopted.

Although the invention has been described above using the above embodiment, the technical scope of the invention is not limited to the scope described in the above embodiment. It is apparent to those skilled in the art that it is possible to make various changes or improvements to the above embodiment. Additionally, it is apparent from the statement of the claims that forms in which such changes or improvements are made can also be included in the technical scope of the invention.

REFERENCE SIGNS LIST

10: HIGH-FREQUENCY TREATMENT TOOL
100: OPERATING PART
110: MAIN BODY
111: SLIT HOLE
112: OUTER PERIPHERAL HOOK
113: INNER TUBE
114: BASE END HOOK
120: TERMINAL PART
121: CONNECTING PORTION
122: ROTATING PORTION
123: POWER SUPPLY TERMINAL
124: FIXING PIN
125: TERMINAL-FIXING PART
126: FLANGE
127: THROUGH-HOLE
128: TERMINAL-REGULATING PART
130: MAIN BODY-OPERATING PART
131: ENGAGING GROOVE
140: SLIDER-GRIPPING PART
141: FIRST COLLAR
142: SECOND COLLAR
143: INTRODUCING PORTION
144: ENGAGING GROOVE
145: INNER CYLINDER SURFACE
150: SLIDER-FIXING PART
151: FIRST FIXING PART
152: SECOND FIXING PART
153: FIRST TAB
154 SECOND TAB
155: FIRST HOOK
1551: ARM
1552: CLAW
156: SECOND HOOK
1561: ARM
1562: CLAW
157: FIRST FLANGE
158: SECOND FLANGE
160: TERMINAL COVER
161: HOOK
170: FINGER-HOOKING PORTION
171: INNER GROOVE
180: CONDUCTIVE PIPE
181: SLIDING TERMINAL
200: FLEXIBLE TUBE
210: COIL PIPE
220: COATING LAYER
250: OPERATING WIRE
300: TREATMENT PART
310: TREATMENT ELECTRODE
320: SUPPORTING SHAFT
330: LINK MECHANISM
340: SUPPORTING FRAME
400: POWER CORD

The invention claimed is:
1. A high-frequency treatment tool comprising:
a flexible tube configured to be inserted into a body cavity;
an operating wire configured to be inserted through the flexible tube so as to be movable back and forth;

a treatment part arranged on a distal end of the operating wire and configured to treat biological tissue by applying a high-frequency current;

a main body configured to rotatably connect to a base end of the flexible tube;

a terminal part rotatably coupled to the main body and including a power supply terminal to which a power cord configured to supply electric power to the treatment part is detachably connected;

a main body-operating part unrotatably coupled to the main body and configured to be gripped when a user rotates the main body;

a slider-fixing part configured to fix a base end of the operating wire guided from the base end of the flexible tube and slide the operating wire in an axis direction with respect to the main body; and a slider-gripping part configured to encircle at least a portion of an outer peripheral surface of the slider-fixing part and slide the slider-fixing part by the operation of the user, wherein the slider-fixing part is unrotatably coupled to the main body and the slider-gripping part is rotatably coupled to the slider-fixing part, the operating wire is configured to be fixed inside the main body, such that rotation of the main body causes the operation wire to rotate inside the flexible tube, and the terminal part is coupled to an end of the main body, which is distal to the main body-operating part and the slider-gripping part.

2. The high-frequency treatment tool according to claim 1, wherein the main body includes a slit hole along the axis direction, wherein the slider-fixing part includes a tab inserted through the slit hole, and wherein the tab fixes the base end of the operating wire and guides sliding of the slider-fixing part along the slit hole.

3. The high-frequency treatment tool according to claim 2, wherein the slider-gripping part forms a cylindrical shape, and wherein the slider-fixing part includes a locking part that is increased in diameter and deformed and engages with the slider-gripping part, rotatably couples the slider-gripping part to the slider-fixing part, and immovably couples the slider-gripping part and the slider-fixing part together in the axis direction of the main body.

4. The high-frequency treatment tool according to claim 2, wherein the main body-operating part, which is thicker than a portion where the slit hole is provided, is formed in a portion of the main body different from the portion where the slit hole is provided in the axis direction.

5. The high-frequency treatment tool according to claim 1, further comprising:

a finger-hooking portion that is rotatably coupled to the main body, at an end portion of the main body, wherein the slider-gripping part has a collar extending in a circumferential direction of the main body.

6. The high-frequency treatment tool according to claim 1, further comprising:

a conductive pipe that covers a portion of the base end of the flexible tube, wherein the flexible tube includes a conductive part that electrically connects the treatment part and the conductive pipe, and wherein the terminal part includes a sliding terminal configured to be in sliding contact with the conductive pipe and supply the electric power from the power cord.

7. The high-frequency treatment tool according to claim 6, wherein the conductive part includes a coil pipe that forms a pipe through which the operating wire is inserted.

8. A method for assembling a high-frequency treatment tool, the high frequency treatment tool comprising:

a flexible tube configured to be inserted into a body cavity;

an operating wire configured to be inserted through the flexible tube so as to be movable back and forth;

a treatment part arranged on a distal end of the operating wire and configured to treat biological tissue by applying a high-frequency current;

a main body configured to rotatably connect to a base end of the flexible tube;

a terminal part rotatably coupled to the main body and including a power supply terminal to which a power cord configured to supply electric power to the treatment part is detachably connected;

a main body-operating part unrotatably coupled to the main body and configured to be gripped when a user rotates the main body;

a slider-fixing part configured to fix a base end of the operating wire guided from the base end of the flexible tube and slide the operating wire in an axis direction with respect to the main body; and a slider-gripping part configured to encircle at least a portion of an outer peripheral surface of the slider-fixing part and slide the slider-fixing part by the operation of the user;

wherein the slider-fixing part is unrotatably coupled to the main body and the slider-gripping part is rotatably coupled to the slider-fixing part;

wherein the operating wire is configured to be fixed inside the main body, such that rotation of the main body causes the operation wire to rotate inside the flexible tube;

wherein the terminal part is coupled to an end of the main body, which is distal to the main body-operating part and the slider-gripping part;

wherein the main body includes a slit hole along the axis direction;

wherein the slider-fixing part includes a tab inserted through the slit hole;

wherein the tab fixes the base end of the operating wire and guides sliding of the slider-fixing part along the slit hole;

wherein the slider-gripping part forms a cylindrical shape; and wherein the slider-fixing part includes a locking part that is increased in diameter and deformed and engages with the slider-gripping part, rotatably couples the slider-gripping part to the slider-fixing part, and immovably couples the slider-gripping part and the slider-fixing part together in the axis direction of the main body, the method comprising:

inserting the slider-fixing part into the slider-gripping part while deforming the locking part toward a radial inner side of the slider-gripping part; and moving the slider-fixing part into a predetermined position, and increasing the diameter of the locking part and deforming the locking part radially outward to couple the slider-gripping part and the slider-fixing part together.

* * * * *